United States Patent [19]
Brooks et al.

[11] 3,947,489
[45] Mar. 30, 1976

[54] COUPLING PROCESS

[75] Inventors: Maurice E. Brooks, Great Neck, N.Y.; Herbert Riegel, Palisades, N.J.; Harvey D. Schindler, New York, N.Y.; Morgan C. Sze, Upper Montclair, N.J.

[73] Assignee: The Lummus Company, Bloomfield, N.J.

[22] Filed: Oct. 23, 1968

[21] Appl. No.: 769,791

[52] U.S. Cl...... 260/488 H; 260/669 R; 260/671 A; 260/671 B; 260/671 M; 260/671 P; 260/671 R; 260/683 R; 260/683.47
[51] Int. Cl.² .......................................... C07C 67/00
[58] Field of Search............ 260/497, 497 A, 488 H, 260/410.9 N

[56] References Cited
UNITED STATES PATENTS 3,221,045   11/1965   McKeon et al. .................... 260/497
3,547,983   12/1970   Mottern et al. ..................... 260/488

*Primary Examiner*—Vivian Garner
*Attorney, Agent, or Firm*—Marn & Jangarathis

[57] ABSTRACT

Process for coupling an alkane to either an alkane, alkene, aliphatic carboxylic acid, or aromatic hydrocarbon by effecting contacting thereof and a melt containing a multivalent metal halide in both its higher and lower valence state. In accordance with a preferred embodiment, the contacting is effected in the presence of an oxygen containing gas or the melt is previously contacted with an oxygen containing gas to produce the corresponding oxyhalide of the metal, whereby the reaction may be effected on a continuous basis.

24 Claims, 1 Drawing Figure

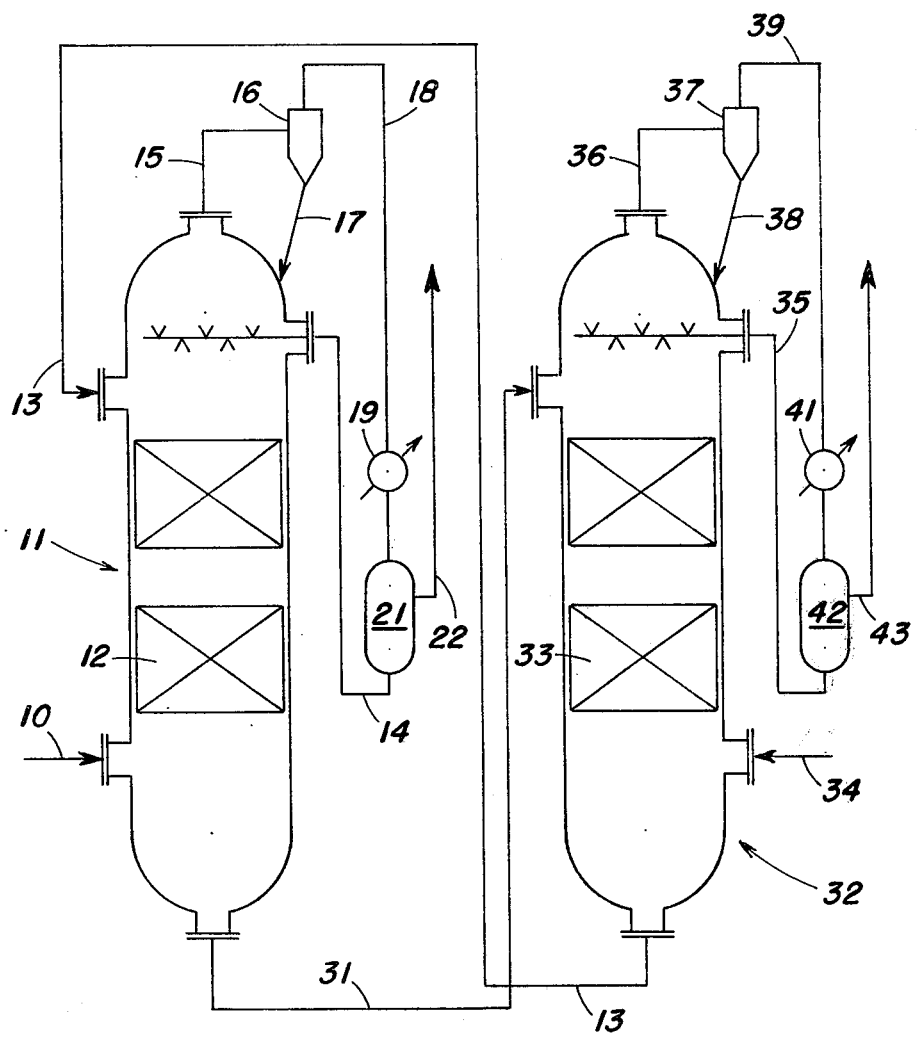

COUPLING PROCESS

This invention relates to a coupling process and more particularly to the production of both saturated and olefinically unsaturated compounds by a coupling reaction.

The production of olefinically unsaturated compounds by a coupling reaction is known in the art; however, in most processes the reaction requires an unsaturated starting material which raises overall costs. Thus, for example, styrene, a valuable polymerization monomer, is produced by reacting benzene with ethylene to produce ethyl benzene which is then dehydrogenated to styrene. As a further example, vinyl acetate, another valuable polymerization monomer is produced by combining acetylene with acetic acid.

Accordingly, an object of this invention is to provide a new and improved coupling process.

Another object of this invention is to produce saturated and olefinically unsaturated compounds by a coupling reaction.

A further object of this invention is to provide a process for coupling two alkanes.

Still another object of this invention is to provide a process for producing ethyl benzene.

A still further object of this invention is to provide a process for producing styrene.

Yet another object of this invention is to provide a process for producing vinyl acetate.

These and other objects of the invention should be more readily apparent from the following detailed description thereof when read with reference to the accompanying drawing wherein:

The drawing is a simplified schematic flow diagram of an embodiment of the invention.

The objects of this invention are broadly accomplished by contacting an alkane with either: another or identical alkane; an olefinically unsaturated compound; an aliphatic carboxylic acid; or an aromatic compound, in the presence of a melt containing a multivalent metal halide in both its higher and lower valence state. The contacting may be effected in the presence of other reagents, as hereinafter described, with reference to preferred embodiments of the invention. As a result of the contacting, a compound is produced containing one portion corresponding to the alkane, with the remainder of the compound corresponding to the other compound employed in the contacting step.

The melt contains a halide of a multivalent metal; i.e., a metal having more than one positive valence state, such as manganese, iron, copper, cobalt and chromium, preferably a chloride or bromide of the metal, with the copper chlorides and bromides, in particular the copper chlorides, being preferred. In the case of higher melting multivalent metal halides, such as copper chlorides, a halide of a univalent metal; i.e., a metal having only one positive valence state, which is nonvolatile and resistant to the action of oxygen under the process conditions is added to the multivalent metal halide to form a molten salt mixture having a reduced melting point. The univalent metal halides, the chlorides and bromides, particularly the chlorides, being preferred, are preferably alkali metal halides, such as potassium and lithium chloride in particular, but it is to be understood that other metal chlorides and mixtures thereof, such as the heavy metal halides of Groups I, II, III and IV of the Periodic Table; e.g., zinc, silver, and thallium chloride, may also be employed. The univalent metal halides are generally added in an amount sufficient to adjust the melting point of the molten salt mixture to a temperature of below about 500°F., and in the case of a salt mixture of copper chloride and potassium chloride, the composition of the melt ranges between about 20% and about 40%, preferably about 30%, by weight, potassium chloride, with the remainder being copper chloride. It is to be understood, however, that in some cases the catalyst melt may have a melting point higher than 500°F., provided the catalyst remains in the form of the melt throughout the processing steps. It is further to be understood that the melt may contain a mixture of multivalent metal halides or other reaction promoters; e.g., a known coupling catalyst, e.g., palladium salt such as palladium chloride, i.e., 0.5–4.0 wt %. It is also to be understood that in some cases the multivalent metal halide (s) may be maintained as a melt without the addition of a univalent metal halide.

The alkane, as hereinabove described, is contacted with either another or identical alkane, preferably a different alkane (isomers containing the same number of carbon atoms are different alkanes), generally an alkane containing no more than about 9 carbon atoms, such as methane, ethane, propane, the various butanes and the like; an olefinically unsaturated compound, generally an alkene containing no more than about 9 carbon atoms, such as ethylene, propylene, the various butenes, and the like; an aliphatic carboxylic acid, generally an alkanoic acid, preferably containing no more than about 5 carbon atoms, such as acetic acid, propionic acid and the like; or an aromatic compound, generally an aromatic hydrocarbon, preferably mononuclear, such as benzene. The feed may contain two or more of such compounds in which case the effluent contains a mixture of products.

The process of the invention results in a coupling of the alkane to the other reactant to produce a combined compound. Thus, the coupling of the alkane: with another or identical alkane results in the production of an alkene and/or alkane, generally a mixture of alkane and alkene containing a number of carbon atoms corresponding to the total number of carbon atoms of the two alkane reactants; with an alkene results in the production of an alkane and/or alkene, generally a mixture of alkane and alkene containing a number of carbon atoms corresponding to the total number of carbon atoms of the alkane and alkene; with an alkanoic acid results in the production of an alkenyl ester of the acid; and with an aromatic hydrocarbon results in the production of an alkenyl and/or alkyl substituted derivative thereof. Thus, for example, the coupling of ethane in accordance with the invention with propane produces pentane and/or pentene; with butylene produces hexane and/or hexene; with propionic acid produces vinyl propionate; and with benzene produces styrene and/or ethyl benzene. Similarly, the coupling of propane with benzene produces cumene and/or propenyl benzene.

It has been found that contacting of the feed to be coupled with the hereinabove described melt results in a net production of hydrogen chloride and a depletion of the content of the higher valent metal chloride, i.e., cupric chloride, in the melt. Therefore, in accordance with one preferred embodiment of the invention, the feed to be coupled is contacted with the melt, containing the multivalent metal halide in both its higher and lower valence state, in the presence of an oxygen-containing gas, such as air. This procedure results in essentially no net production of hydrogen chloride and maintains the higher valent metal halide content of the melt substantially constant.

As an alternative procedure to the hereinabove described preferred embodiment, the melt containing a mixture of a multivalent metal halide in both its higher and lower valence state may be initially contacted with oxygen and the resulting product, containing the corresponding oxyhalide of the multivalent metal, is then contacted with the feed to be coupled. This procedure also results in essentially no net production of hydrogen chloride and a substantially constant content of cupric chloride and is of greater commercial value in that oxygen does not contact the feed, thereby decreasing any losses which may result from combustion of the feedstock.

As a further embodiment, the feed to be coupled is contacted with the melt, containing the multivalent metal halide in both its higher and lower valence state, in the presence of a free-halogen containing gas, corresponding to the halide of the multivalent metal. This procedure although maintaining essentially no net loss of cupric chloride, results in a net production of hydrogen chloride and consequently is less preferred than the hereinabove described preferred embodiment. It is to be understood that similarly to the preferred embodiment, the melt may be contacted with the free halogen containing gas separately from the coupling step to replenish the cupric chloride content of the melt.

As a further alternative embodiment, the hydrogen chloride generated in the coupling reaction, may be recovered from the effluent and employed along with an oxygen-containing gas to contact the cupric chloride depleted melt to regenerate cupric chloride for the subsequent coupling step. This procedure is also less preferred, but may be employed within the scope of the invention.

The various contacting steps including contacting of the melt with oxygen, chlorine, or hydrogen chloride, as hereinabove described are generally effected at temperatures from about 500° to about 1200°F. and pressures from about 1 to about 30 atmospheres. The contacting is preferably effected in a countercurrent fashion, with the feed as a continuous vapor phase, at residence times between about 1 and about 100 seconds. The choice of optimum reaction conditions varies with the particular reactants and desired reaction products, and, therefore, the hereinabove described conditions are illustrative of the invention and the scope thereof is not to be limited thereby. Thus, for example, in the coupling of ethane to benzene, ethyl benzene is generally produced at temperatures from about 500° to about 1000°F. and styrene at temperatures from about 700° to about 1200°F., with a mixture of ethyl benzene and styrene being produced at the overlapping portions of the temperature range; i.e., from about 700° to about 1000°F. It is further to be understood that by-products are also produced during the reaction and, therefore, the reaction conditions are controlled to reduce such production. The separation of the resulting by-products in order to recover the desired product may be effected by a wide variety of well-known procedures and, therefore, no detailed explanation thereof is deemed necessary.

It should be further apparent from the hereinabove description of the invention that the melt containing the multivalent metal halide participates in the reaction sequence and accordingly does not behave solely as a catalyst. Therefore, the multivalent metal halides must be present in an amount sufficient to meet reaction requirements and in general the melt composition should contain at least 3%, by weight, of the higher valent halide, although greater amounts are preferred. In some cases, the addition of chlorine may be required in order to maintain the necessary quantity of cupric chloride.

The melt in addition to functioning as a reactant and/or catalyst is a temperature regulator. Thus, the circulating melt has a high heat absorption capacity thereby preventing runaway reaction during the exothermic coupling and oxygen contacting steps. The absorbed heat of reaction may be employed to heat the various reactants to reaction temperature. Alternatively, or in addition to such an expedient, the melt may be contacted with an inert gas coolant to remove any additional heat of reaction, with the inert gas being subsequently cooled and re-employed for removing heat from the melt. It should be apparent, however, that if additional heat is required such heat may be supplied from an external source.

The invention will now be further described with reference to an embodiment thereof illustrated in the accompanying drawing. It is to be understood, however, that the scope of the invention is not to be limited thereby.

Referring now to the drawing, an oxygen-containing gas in line 10, such as air, is introduced into a reactor 11, containing suitable packing 12 or other liquid-vapor contacting devices. A melt containing a multivalent metal halide in both its higher and lower valence state, such as a mixture of cupric and cuprous chloride, is introduced into reactor 11 through line 13 in the form of a melt and countercurrently contacts the ascending oxygen-containing gas. The melt may further contain an alkali metal chloride, such as potassium chloride. As a result of such contact, a portion of the cuprous chloride is exothermically converted to copper oxychloride.

An oxygen depleted gas in the top of the reactor 11 is contacted with a quench liquid introduced through line 14, resulting in condensation of vaporized melt and vaporization of quench liquor. The vaporized quench liquid and oxygen-depleted gas is withdrawn from reactor 11 through line 15 and introduced into a cyclone separator 16 to effect separation of entrained catalyst. The separated catalyst is withdrawn from separator 16 through line 17 and returned to the reactor 11. The combined oxygen-depleted gas-vaporized quench liquid is withdrawn from separator 16 through line 18, passed through condenser 19 to effect condensation of the quench liquid and the vapor-liquid mixture introduced into a separator 21. The quench liquid is withdrawn from separator 21 in line 14 and recycled to the reactor 11. The oxygen-depleted gas is withdrawn from separator 21 through line 22 and passed to waste.

The melt-containing a mixture of cuprous chloride, cupric chloride and copper oxychloride is withdrawn from reactor 11 through line 31 and introduced into the top of a coupling reactor 32, containing suitable packing 33 or other gas-liquid contacting devices. A feed to be coupled, such as ethane and acetic acid, is introduced into the bottom of vessel 32 through line 34 and countercurrently contacts the descending melt to effect coupling of the feed. The melt withdrawn from the bottom of vessel 32 through line 13 is recycled to reactor 11.

A gaseous effluent containing vinyl acetate and by-products, is contacted in the top of vessel 32 with a quench liquid introduced through line 35, resulting in condensation of vaporized catalyst melt and vaporization of the quench liquid. The vaporized quench liquid and effluent is withdrawn from vessel 32 through line 36 and introduced into a cyclone separator 37 to effect removal of entrained catalyst. The separated catalyst is withdrawn from separator 37 through line 38 and recycled to the vessel 32. The vaporized quench liquid and gaseous effluent are withdrawn from separator 37 through line 39, passed through condenser 41 to effect condensation and cooling of the quench liquid and the gas-liquid mixture is introduced into a separator 42. The now cooled quench liquid is withdrawn from separator 42 through line 35 and recycled to the reactor 32. The effluent is withdrawn from separator 42 through line 43 and passed to separation and recovery.

It is to be understood that numerous variations of the hereinabove described processing sequence are possible within the spirit and scope of the invention. Thus, for example, the coupling reaction may be effected in a single reactor having two separate zones, one for the introduction of an oxygen-containing gas for contact with the melt and the other for contacting the resulting oxygenated melt with the feed to be coupled. Alternatively, as hereinabove described, the melt containing the multivalent metal halide in both its higher and lower valence state, may be contacted with a mixture of an oxygen-containing gas and a feed to be coupled. Similarly, a halogen containing gas, such as chlorine, may be employed instead of an oxygen-containing gas in which case as hereinabove described, there is a net production of hydrogen chloride. These and other modifications should be apparent to those skilled in the art from the teachings contained herein.

The invention is further illustrated by the following examples but the scope of the invention is not to be limited thereby.

EXAMPLE I

Ethane and acetic acid are coupled by countercurrently contacting an ethane-acetic acid mixture with a copper chloride containing melt which has previously been contacted with air, under the following conditions:

| | |
|---|---|
| Reaction Temperature | 395°C. |
| Reaction Pressure | 1 atm |
| Molten Salt | |
| KCl | 30 wt % |
| CuCl | 55 wt % |
| $CuCl_2$ | 15 wt % |
| Residence Time | 11 seconds |
| Duration of Test | 1.5 hours |
| Gas Hourly Space Velocity, GHSV | 75 |
| Feed Rate, gm-mole/hr | |
| $C_2H_6$ | 0.22 |
| Acetic Acid | 0.10 |
| Percent Vinyl acetate in liquid product | 4.5% |

EXAMPLE II

Ethane and benzene are coupled under the following conditions by countercurrently contacting an ethane-benzene mixture with a copper chloride containing melt which has previously been contacted with air.

| | |
|---|---|
| Reaction Temperature | 355°C. |
| Reaction Pressure | 1 atm |
| Molten Salt | |
| KCl | 30 wt % |
| CuCl | 40 wt % |
| $CuCl_2$ | 30 wt % |
| Residence Time | 9.0 sec. |
| Duration of Test | 3 hours |
| Gas Hourly Space Velocity, GHSV | 83 |
| Feed Rate, gm-mole/hr | |
| Ethane | 0.67 |
| Benzene | 0.39 |
| Ethane Conversion | 5.0% |

The reaction product contains mainly ethyl benzene and some styrene.

EXAMPLE III

The procedure of Example II is repeated except that the temperature is raised to 483°C.

The reaction product contains mainly styrene and some ethyl benzene.

EXAMPLE IV

Isobutane is coupled to n-butane by contacting a mixture thereof with a copper chloride melt under the following conditions:

| | |
|---|---|
| Reaction Temperature | 386°C. |
| Reaction Pressure | 1 atm |
| Molten Salt | |
| KCl | 30 wt % |
| CuCl | 45 wt % |
| $CuCl_2$ | 25 wt % |
| Residence Time | 10 sec. |
| Duration of Test | 3 hours |
| Gas Hourly Space Velocity, GHSV | 79 |
| Feed Rate, gm-mole/hr | |
| Isobutane | 0.23 |
| n-Butane | 0.23 |
| Isobutane Conversion | 16% |

The reaction product contains $C_8$ alkanes and alkenes.

EXAMPLE V

The procedure of Example IV is repeated except that the feed is a mixture of pentane and propylene.

The reaction product is a mixture of $C_8$ alkanes and alkenes.

EXAMPLE VI

The procedure of Example I is repeated except that the melt has the following composition:

| | |
|---|---|
| $FeCl_2$ | 58 wt % |
| $FeCl_3$ | 8 wt % |
| KCl | 34 wt % |

The reaction product contains vinyl acetate.

EXAMPLE VII

The procedure of Example III is repeated except that the melt has the following composition:

| | |
|---|---|
| $MnCl_2$ | 3 wt % |
| $MnCl_4$ | 80 wt % |
| KCl | 17 wt % |

The reaction product contains mainly styrene and some ethyl benzene.

EXAMPLE VIII

The procedure of Example II is repeated except that the melt has the following composition:

| | |
|---|---|
| $CoCl_2$ | 14 wt % |
| $CoCl_3$ | 49 wt % |
| KCl | 37 wt % |

The reaction product contains mainly ethyl benzene and some styrene.

EXAMPLE IX

The procedure of Example IV is repeated except that the temperature is 483°C. and the melt has the following composition:

| | |
|---|---|
| $CrCl_2$ | 5 wt % |
| $CrCl_3$ | 74 wt % |
| KCl | 21 wt % |

The reaction product contains $C_8$ alkanes and alkenes.

EXAMPLE X

The procedure of Example II is repeated except that the feed contains propane and benzene.

The reaction product contains cumene.

EXAMPLE XI

The procedure of Example I is repeated except that the melt includes a palladium chloride promoter. The melt has the following composition.

| | |
|---|---|
| KCl | 24 wt % |
| CuCl | 55 wt % |
| $CuCl_2$ | 15 wt % |
| $PdCl_2$ | 3 wt % |

The reaction product contains vinyl acetate.

The hereinabove examples are also repeated with bromides and iodides of the multivalent metals with similar results.

The process is extremely advantageous in that olefinically unsaturated compounds may be produced in a single reactor. As a further advantage, valuable products such as styrene, ethyl benzene, and vinyl acetate may be produced in a single reactor without using an unsaturated compound as a starting material. These and other advantages of the invention should be readily apparent to those skilled in the art.

Numerous modifications and variations in the present invention are possible in light of the above teachings and, therefore, it is to be understood that the invention may be practiced otherwise than as particularly described.

What is claimed is:

1. A process for coupling an alkane having no more than nine carbon atoms with an alkanoic acid having no more than five carbon atoms, comprising:

contacting the alkane and the alkanoic acid, both in the vapor phase, with a molten mixture comprising the higher and lower valent forms of a multivalent metal halide selected from the group consisting of the chlorides, iodides, and bromides of copper, manganese, iron, cobalt and chromium, said higher valent metal halide being present in an amount of at least 3 weight percent, said contacting being effected at a temperature from about 500°F. to about 1200°F. to produce a coupled compound which is the alkenyl ester of the alkanoic acid having a number of carbon atoms corresponding to the total number of carbon atoms in said alkane and said alkanoic acid.

2. The process of claim 1 wherein the multivalent metal halide is a copper chloride.

3. A process for coupling an alkane having no more than nine carbon atoms with an alkanoic acid having no more than five carbon atoms, comprising:

contacting oxygen, the alkane and the alkanoic acid, both in the vapor phase, with a molten mixture comprising the higher and lower valent forms of a multivalent metal halide selected from the group consisting of the chlorides, iodides, and bromides of copper, manganese, iron, cobalt and chromium, said higher valent halide being present in an amount of at least 3 wt. %, said contacting being effected at a temperature from about 500° to about 1200°F. to produce a coupled compound which is the alkenyl ester of the alkanoic acid having a number of carbon atoms corresponding to the total number of carbon atoms in said alkane and said alkanoic acid.

4. The process of claim 3 wherein the multivalent metal halide is a copper chloride.

5. A process for coupling an alkane having no more than nine carbon atoms with an alkanoic acid having no more than five carbon atoms, comprising:

contacting the alkane and the alkanoic acid, both in the vapor phase, with a molten mixture comprising the higher and lower valent forms of a multivalent metal halide and the oxyhalide of said multivalent metal wherein said halide is selected from the group consisting of the chlorides, iodides, and bromides and said multivalent metal is selected from the group consisting of copper, manganese, iron, cobalt, and chromium, said higher valent halide being present in an amount of at least 3 weight percent, said contacting being effected at a temperature from about 500° to about 1200°F. to produce a coupled compound which is the alkenyl ester of the alkanoic acid having a number of carbon atoms corresponding to the total number of carbon atoms in said alkane and said alkanoic acid.

6. The process of claim 5 wherein the multivalent metal halide (and) is a chloride and the multivalent metal oxyhalide (are a chloride and) is an oxychloride. (respectively)

7. The process of claim 6 wherein the contacting in the vapor phase is effected in the absence of molecular oxygen.

8. The process of claim 6 wherein the alkane is ethane, and the alkanoic acid is acetic acid and the coupled compound is vinyl acetate.

9. A process for coupling an alkane having no more than nine carbon atoms with an alkanoic acid having no more than five carbon atoms, comprising:

contacting the alkane and the alkanoic acid, both in the vapor phase, with a molten mixture consisting essentially of the higher and lower valent forms of a multivalent metal halide selected from the group consisting of the chlorides, iodides, and bromides of copper, manganese, iron, cobalt and chromium, said higher valent halide being present in an amount of at least 3 weight percent, said contacting being effected at a temperature from about 500° to about 1200°F. to produce a coupled compound which is the alkenyl ester of the alkanoic acid having a number of carbon atoms corresponding to the total number of carbon atoms in said alkane and said alkanoic acid.

10. The process of claim 9 wherein the multivalent metal halide is a chloride.

11. The process of claim 10 wherein the molten mixture includes as a melting point depressant a member selected from the group consisting of alkali metal chlorides and the chlorides of the heavy metals of Groups I, II, III and IV of the Periodic Table.

12. The process of claim 10 wherein said alkane is ethane, said alkanoic acid is acetic acid and said coupled compound is vinyl acetate.

13. The process of claim 12 wherein the higher and lower valent metal chlorides are cuprous and cupric chloride and the molten mixture further includes, as a melting point depressant, potassium chloride.

14. A process for coupling an alkane having no more than nine carbon atoms with an alkanoic acid having no more than five carbon atoms, comprising:
contacting oxygen, the alkane and the alkanoic acid, both in the vapor phase, with a molten mixture consisting essentially of the higher and lower valent forms of a multivalent metal halide selected from the group consisting of the chlorides, iodides, and bromides of copper, manganese, iron, cobalt and chromium, said higher valent halide being present in an amount of at least 3 weight percent, said contacting being effected at a temperature from about 500° to about 1200°F. to produce a coupled compound which is the alkenyl ester of the alkanoic acid having a number of carbon atoms corresponding to the total number of carbon atoms in said alkane and said alkanoic acid.

15. The process of claim 14 wherein the multivalent metal halide is a chloride.

16. The process of claim 15 wherein the molten mixture includes as a melting point depressant a member selected from the group consisting of alkali metal chlorides and the chlorides of the heavy metals of Groups I, II, III and IV of the Periodic Table.

17. The process of claim 15 wherein said alkane is ethane, said alkanoic acid is acetic acid and said coupled compound is vinyl acetate.

18. The process of claim 17 wherein the higher and lower valent metal chlorides are cuprous and cupric chloride and the molten mixture further includes, as a melting point depressant, potassium chloride.

19. A process for coupling an alkane having no more than nine carbon atoms with an alkanoic acid having no more than five carbon atoms, comprising:
contacting the alkane and the alkanoic acid, both in the vapor phase with a molten mixture consisting essentially of the higher and lower valent forms of a multivalent metal halide and the oxyhalide of said multivalent metal wherein said halide is selected from the group consisting of the chlorides, iodides, and bromides and said multivalent metal is selected from the group consisting of copper, manganese, iron, cobalt and chromium, said higher valent halide being present in an amount of at least 3 weight percent, said contacting being effected at a temperature from about 500° to about 1200°F. to produce a coupled compound which is the alkenyl ester of the alkanoic acid having a number of carbon atoms corresponding to the total number of carbon atoms in said alkane and said alkanoic acid.

20. The process of claim 19 wherein the multivalent metal halide is a chloride and the multivalent metal oxyhalide is an oxychloride.

21. The process of claim 20 wherein the molten mixture includes as a melting point depressant a member selected from the group consisting of alkali metal chlorides and the chlorides of the heavy metals of Groups I, II, III and IV of the Periodic Table.

22. The process of claim 20 wherein said multivalent metal halides are copper chlorides and said oxychloride is copper oxychloride.

23. The process of claim 22 wherein said alkane is ethane, said alkanoic acid is acetic acid and said coupled compound is vinyl acetate.

24. The process of claim 23 wherein the higher and lower valent metal chlorides are cuprous and cupric chloride, the oxychloride of the multivalent metal is copper oxychloride and the melt further includes, as a melting point depressant, copper oxychloride.

* * * * *